United States Patent [19]

Nakayama et al.

[11] Patent Number: 4,744,752
[45] Date of Patent: May 17, 1988

[54] DENTAL HANDPIECE CONTROL DEVICE

[75] Inventors: Shozo Nakayama; Hiroo Watanabe; Toshiki Tawa, all of Kyoto; Shusuke Hashimoto, Osaka; Katsumi Suzuki; Teruji Nakai, both of Kyoto, all of Japan

[73] Assignee: Kabushiki Kaisha Morita Seisakusho, Kyoto, Japan

[21] Appl. No.: 759,606

[22] Filed: Jul. 26, 1985

[30] Foreign Application Priority Data

Jul. 30, 1984 [JP] Japan .................. 59-160742
Jul. 30, 1984 [JP] Japan .................. 59-160743
Sep. 18, 1984 [JP] Japan .............. 59-141303[U]
Sep. 18, 1984 [JP] Japan .............. 59-141304[U]

[51] Int. Cl.⁴ .............................................. A61C 1/02
[52] U.S. Cl. ..................................... 433/100; 433/98; 433/101; 433/132
[58] Field of Search ................. 433/100, 101, 99, 98, 433/132

[56] References Cited

U.S. PATENT DOCUMENTS 3,947,965  4/1976  Flatland ................ 433/100
4,494,933  1/1985  Matsui .................. 433/98

FOREIGN PATENT DOCUMENTS 1107891  5/1961  Fed. Rep. of Germany ........ 433/99
  52501  5/1981  Japan ............................. 433/101

Primary Examiner—John J. Wilson
Attorney, Agent, or Firm—Koda and Androlia

[57] ABSTRACT

A control device for use in an air turbine dental handpiece comprising an air turbine which is integrated with a spindle supporting a cutting tool and is rotatably supported in a head housing by bearings, an air supply passage which supplies compressed air to the air turbine and an exhaust passage which discharges air spent to drive the air turbine, the control device being characterized in that the control device comprises a pressure or flowrate regulating device disposed in the exhaust passage to control the speed of the turbine in the range of stop to high-speed operation by changing the back pressure of the air turbine.

17 Claims, 13 Drawing Sheets

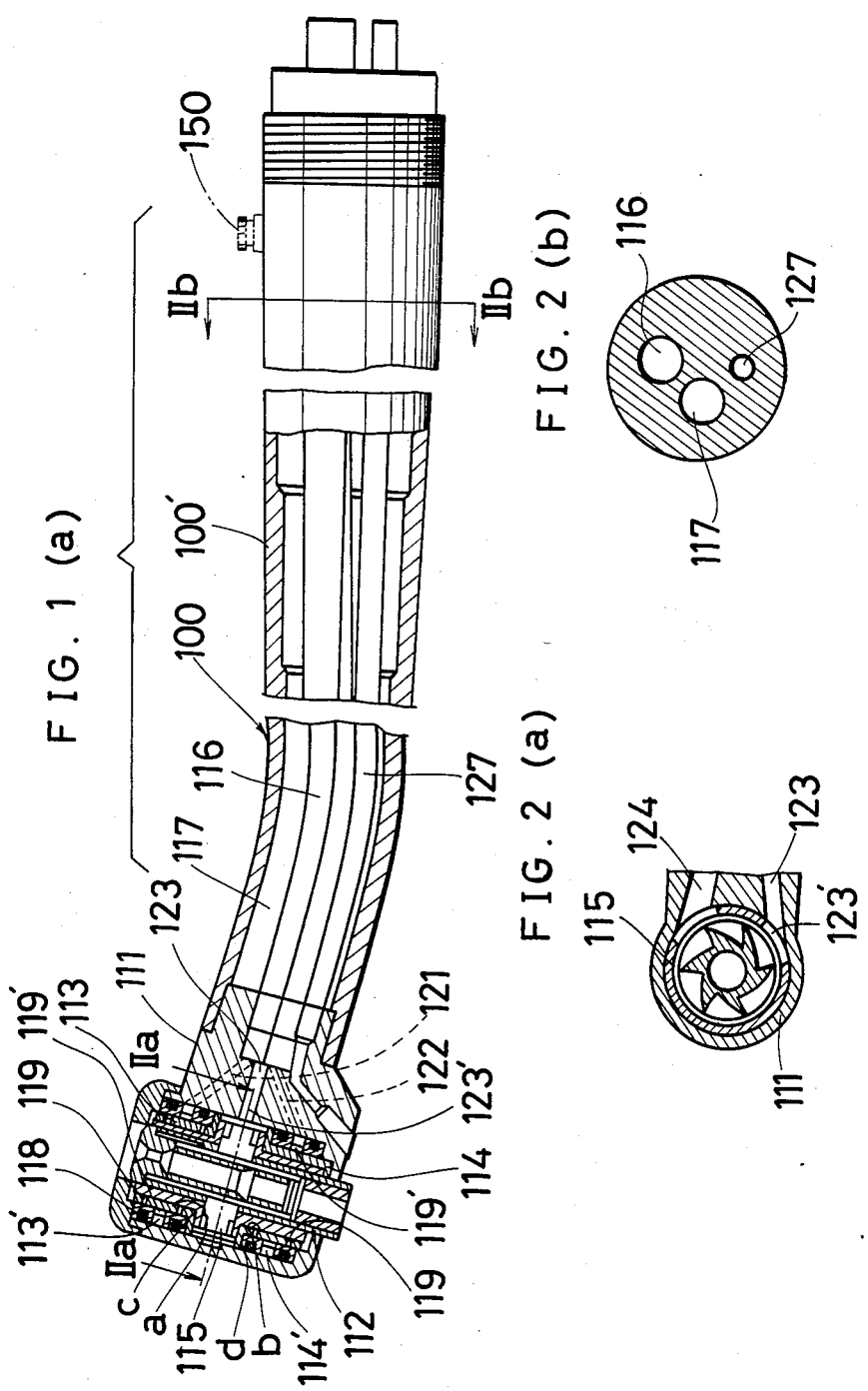

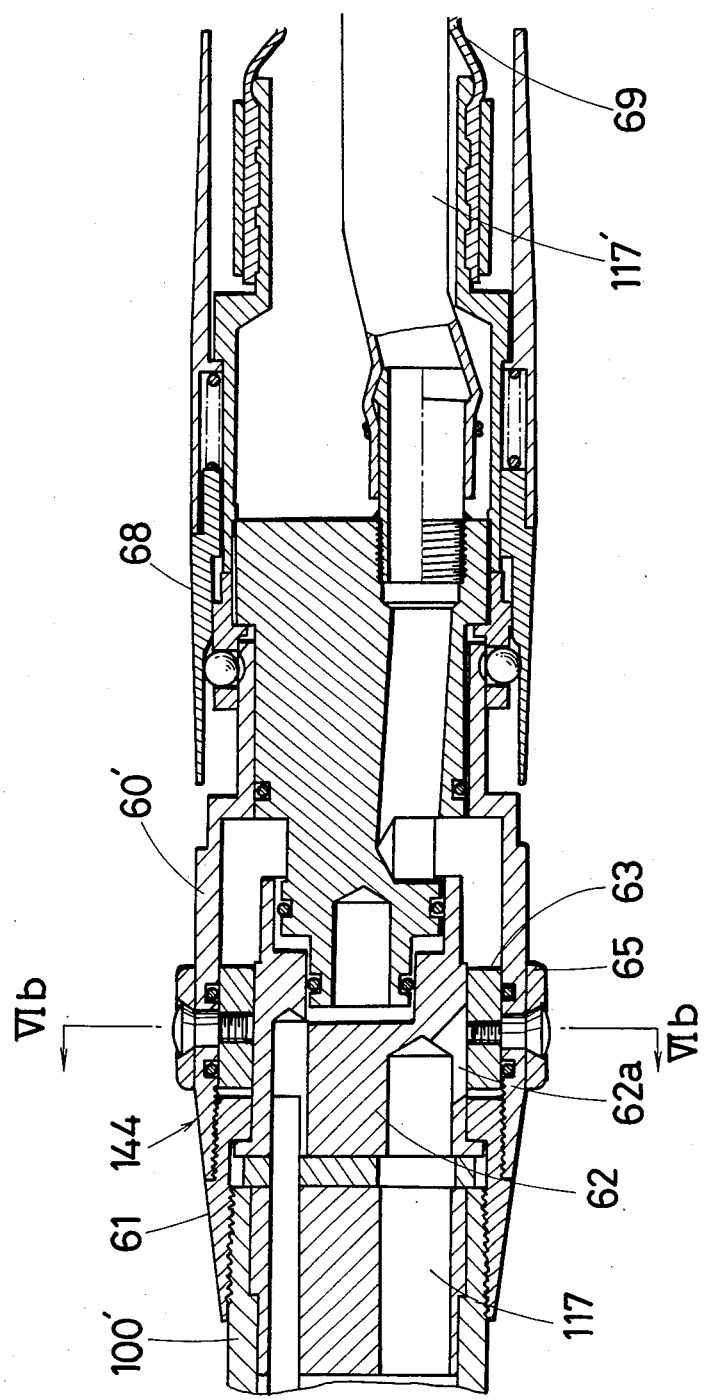

DENTAL HANDPIECE CONTROL DEVICE

BACKGROUND OF THE INVENTION

1. Field of the Invention

The present invention relates to a dental handpiece control device, and more particularly to a dental handpiece control device including a pressure regulating device or a flowrate regulating device to control the speed of an air turbine by changing the back pressure of the air turbine in a leakless exhaust passage which discharges air spent to drive the air turbine into atmosphere.

2. Prior Art

An air turbine handpiece has long been used particularly in dental treatment to remove decayed portions by high-speed cutting or to improve the surface roughness of teeth after abutment formation and to form margins by low-speed cutting. For low-speed control, a known handpiece with an air turbine uses a control device disposed in an air supply passage as shown in FIG. 12 for example, as disclosed in Japanese Patent Provisional Publication No. 57-6939 and Japanese Utility Model Provisional Publication No. 59-15618. More specifically, compressed air from a compressed air source 410 passes through a filter 420 and the pressure of the compressed air is reduced by a fixed-amount pressure regulating valve 430 to the pressure specified for a handpiece. The compressed air passes through an air tube 4 and is supplied to a pressure regulating valve or a flowrate regulating valve 440. The pressure of the compressed air is further reduced by the valve and supplied to an air turbine handpiece 450. When the regulating valve is fully opened, the pressure set by the pressure regulating valve 430 is supplied. The flowrate regulating valve 440 is generally controlled by a foot pedal so that the dentist can obtain the speed suited for treatment.

A dental handpiece having a construction to rapidly stop the air turbine has been disclosed by Japanese Patent Provisional Publication No. 46-31519 and Japanese Utility Model Provisional Publication No. 56-124413. The former has two 3-way solenoid valves and a circuit delay relay. In case of stopping the air turbine by controlling a foot switch, compressed air to the air passage is stopped by one of the 3-way solenoid valves and compressed air begins to be supplied through the other solenoid valve from the compressed air source to the exhaust passage to brake the turbine. After the turbine is stopped, the relay functions so that the air supply passage which was shut off by the valve is opened to discharge the remaining air to atmosphere after the lapse preset time. The latter is an improvement of the former, that is, fluctuation of delay operation due to the deterioration of the relay or changes in temperature and humidity is reduced so that the turbine can be stopped in the minimum time.

Referring to FIG. 13, an air timer 315 is used in instead of the delay relay. When stopping is begun by releasing a foot switch 320, a four-way solenoid valve 302 is switched to supply compressed air from a compressed air source 301 to the exhaust passage 317 of a handpiece 300 and to brake the turbine of the handpiece. At the same time, the air supply passage 316 is opened to atmosphere. After a specified time, a pilot valve 310a is activated to stop supplying compressed air to the exhaust passage 317 as shown in FIG. 13. As a result, compressed air is jetted to the rear of the turbine so that compressed air can be supplied to the bearing mechanism even when the turbine is braked. This prevents dust from entering the bearing mechanism due to buildup pressure in the mechanism. However, these prior arts have the following defects.

As detailed in the hydrodynamic analysis description below, when the turbine speed is intended to be lowered by reducing the air supply pressure at the air supply passage, exhaust air from the turbine expands until the pressure of the exhaust air reaches atmospheric pressure with almost no resistance and is discharged. As a result, it is impossible to control the pressure of high-speed air jetted from the turbine nozzle and thus the rotation torque of the turbine decreases drastically. Therefore, turbine speed control by regulating air supply pressure is not suited for dental treatment which needs a relatively high rotation torque at low speed. Furthermore, the load capacity and rigidity of the bearings decrease since air supply pressure is reduced to rotate the turbine at low speed in the conventional handpiece with an air turbine of a pneumatic bearing type.

Moreover, since compressed air for braking is supplied from the exhaust passage and discharged from the air supply passage during braking, the air pressure in the air supply ports for the bearings drops when the air supply pressure drops. As a result, the bearing clearance in the thrust direction is not properly obtained and metal contact is caused. Moreover, since compressed air is supplied from the exhaust passage, the bearing clearance in the radial direction becomes eccentric and metal contact is also caused. Thus, wear of parts is hastened. The clearance in the radial direciton used to regulate the rotation center of the turbine is a very small value of 5 to 15$\mu$, and the size of the clearance is determined depending on the shapes of the air supply ports and bearings. Since the dimensional allowance of the clearance is very small (high-speed of 500,000 rpm is obtained when the inner diameter of the air supply ports is 0.18 mm, and the clearance in the radial direction is 10.5$\mu$), the bearing performance is significantly lowered eve if the handpiece parts are worn only 1 to 2$\mu$. When the handpiece is used after the handpiece parts have been worn, the turbine speed drops and greater noise is generated.

SUMMARY OF THE INVENTION

The control device of the dental handpiece of the present invention comprises an air turbine which is integrated with a spindle supporting a cutting tool and is rotatably supported in the head housing by bearings, an air supply passage which supplies compressed air to the air turbine and an exhaust passage which discharges the air spent to drive the air turbine wherein a pressure regulating device or a flowrate regulating device is disposed in the exhaust passage to change the back pressure of the air turbine.

It is therefore an object of the present invention to provide a control device whereby significant drop of rotation torque at low speed rotation of the air turbine as observed in the conventional handpiece is minimized for higher cutting performance at low speed, and the load capacity and rigidity of the pneumatic bearings of the air turbine handpiece are maintained even at low speed.

It is another object of the present invention to provide a control device which can rapidly stop the air turbine using friction caused by closing the exhaust passage, by stopping air flow in the clearance in the thrust direction and by generating negative bearing rigidity while maintaining proper bearing performance in the radial direction by supplying compressed air into the clearance in the radial direction even during braking.

Generally, rotation torque T is a monotone increasing function relative to mass flowrate g per unit time and relative velocity v of high-speed fluid jetted from the nozzle to the turbine blades as indicated in the formula (1) below.

$$T = \alpha f(g.v) \ldots \quad (1)$$

where $\alpha$ is a constant dependent on the shapes of the nozzle and turbine blades.

The velocity v of the high-speed fluid is defined as follows.

$$v = u - 2\pi n r \ldots \quad (2)$$

where u is the velocity of high-speed fluid jetted from the nozzle, n is the turbine speed per unit time and r is the turbine blade radius.

When no load is applied, that is, T=0, u=2 $\mu$nr and thus the following formula is introduced.

$$n = u/(2\pi r) \ldots \quad (3)$$

This means that the speed n under no load is a function of only the jet speed u of the high-speed fluid jetted from the turbine nozzle after the geometrical shape of the handpiece has been determined.

Accordingly, the speed can be controlled by changing the jet speed. In the case of the conventional method, the jet speed in the formula (3) is changed by changing the air supply pressure using the flowrate regulating valve 440 as described above. However, this method causes a problem as described below. The nozzle jet velocity u is hydrodynamically represented as follows.

$$u = a_0 \sqrt{\frac{2}{\gamma - 1}\left(1 - \left(\frac{P}{P_o}\right)^{(\gamma-1)/\gamma}\right)} \quad (4)$$

where $a_o$ is the speed of sound at the branch point and is equal to $\sqrt{\gamma P o \rho o}$, Po is pressure in the branch position (is almost equal to the pressure reduced by the flowrate regulating valve 440 in the case of the conventional example), r is specific heat (approximately 1.40 in the case of air), P is pressure of high-speed fluid jetted just behind the nozzle (pressure just behind the turbine nozzle in this case, that is, pressure in the head), and $\rho_o$ is density at the branch point. Referring to the formula (4), if Po is lowered just as used in the conventional method in order to decrease the rotation speed, that is, flow velocity u, $a_o$ and the value in the root are lowered.

However, this method has the following defects. The power to rotate the turbine is given by the product of flow velocity and flowrate per unit time. If the air supply pressure (almost equal to Po) drops, density $\rho$ is also lowered. Thus, q=$\rho$uA is established. Accordingly, the flowrate lowers when flow velocity drops and the flowrate also lowers when density $\rho$ drops. As a result, the flowrate is drastically lowered.

On the other hand, in the case of the control device of the present invention which controls the rotation speed by increasing the back pressure of an air turbine, P in the formula (4), using a pressure regulating device or a flowrate regulating device in the exhaust passage, the jet velocity u is decreased by increasing the density $\rho$ rather than by decreasing the density. Thus, the drop of torque T at low speed is fairly limited.

In the case of the handpiece with an air turbine of a pneumatic bearing type, the rotation speed is lowered by throttling the exhaust passage. Thus, the load capacity and rigidity of bearings can be maintained at higher values in a wide speed range than those of conventional handpieces. That is, the compressed air supplied from the air supply passage is spent in the handpiece. Even when an opening and shutting device or a flowrate regulating device in the exhaust passage is closed and thus the exhaust passage is shut off to stop the turbine, the compressed air is still supplied into the bearing clearance in the radial direction so that the bearings can perform properly in the radial direction.

To rapidly stop the turbine, the exhaust passage is completely closed. Thus, the flow of exhaust air is stopped, and the pressure in the head housing is prevented from dropping. As a result, external air cannot enter the bearings, preveitnig entry of fine particles into the bearings. In addition, the air flow in the clearance of the pneumatic bearings in the thrust direction is stopped to generate negative bearing rigidity at the thrust bearing section so that the turbine can be rapidly stopped by friction. The clearance in the thrust direction is approximately 40 to 70$\mu$. Therefore, the bearing performance is not greatly affected even if the thrust bearing surfaces are worn approximately 10$\mu$.

BRIEF DESCRIPTION OF THE DRAWINGS

The objects of the present invention will become more apparent when preferred embodiments are considered in connection with the drawings.

FIG. 1 (b) is a control circuit diagram of the first embodiment of the present invention;

FIG. 1 (c) is a control circuit diagram of the second embodiment of the present invention;

FIG. 2 (a) is a sectional view taken substantially along the line IIa—IIa of FIG. 1 (a);

FIG. 2 (b) is a sectional view taken substantially along the line IIb—IIb of FIG. 1 (a);

FIG. 4 (b) is a plan view of the regulating device;

FIG. 6 (b) is a sectional view taken substantially along the line VIb—VIb of FIG. 6 (a);

FIG. 6 (c) is a drawing to explain the full-open setting of the regulating device of FIG. 6 (b) which illustrates the closing condition of the regulating device;

FIG. 9 (b) is a control circuit diagram of the fourth embodiment of the present invention;

FIG. 9 (c) is a control circuit diagram of the fifth embodiment of the present invention;

FIG. 11 (b) is a control circuit diagram of the seventh embodiment of the present invention suited for rapid stop control;

DETAILED DESCRIPION OF THE INVENTION (Description of the Preferred Embodiments)

Figure 1:
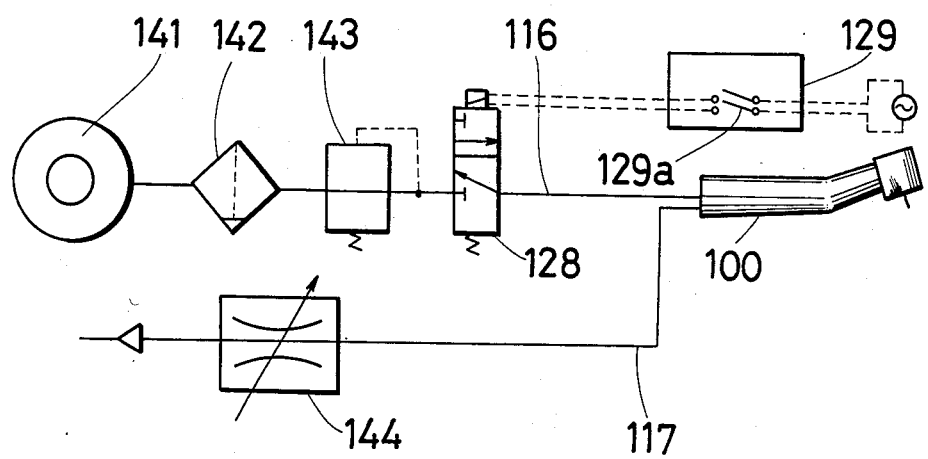
FIG. 1 (a) is a vertical sectional view of of a pneumatic bearing type dental handpiece suited for application of the embodiments of the present invention.
Figure 1:
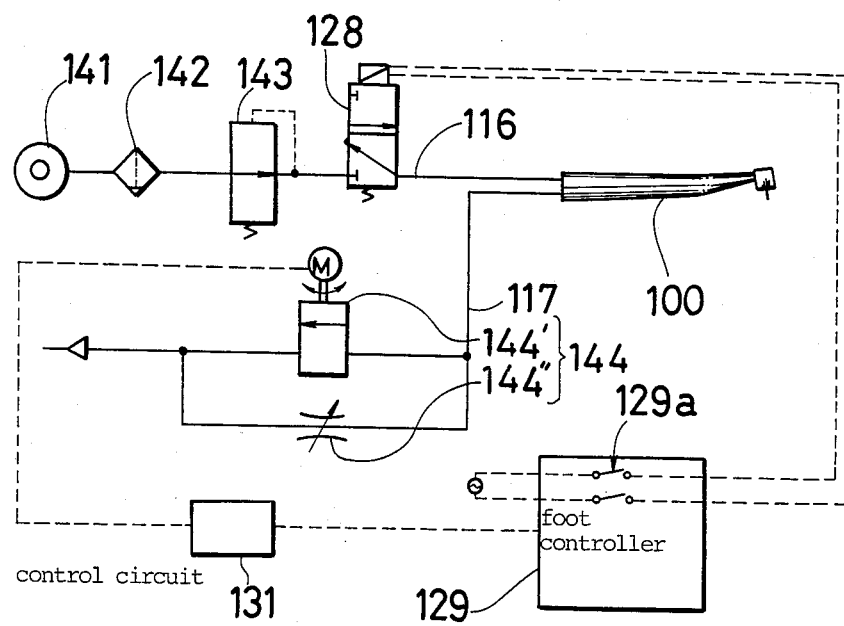

Referring to FIG. 1 (a), a pneumatic bearing type dental handpiece 100 comprises an air turbine 115 which is integrated with a spindle supporting a cutting tool and is rotatably supported by a pair of upper and lower bearings 113 and 114 in a head housing 111, an air supply passage 116 which supplies compressed air to the air turbine 115 and a leakless and nonbleeding exhaust passage 117 which is used to discharge the compressed air spent to drive the air turbine. Very small clearances are provided between the air turbine 115 and the bearings 113 and 114. A pair of upper and lower O-rings 118 are disposed so that a bearing air groove 113' disposed in the middle of the bearing 113 is positioned between the pair of the O-rings, and another pair of upper and lower O-rings are disposed so that a bearing air groove 114' disposed at the middle of the bearing 114 is positioned between the pair of the O-rings. These O-rings 118 are used to airtightly seal the areas between the head housing 111 and the bearings 113 and 114. Therefore, the bearing air grooves 113' and 114' are also airtightly sealed.

A plurality of air supply ports are formed in the bearings 113 and 114 in the radial direction. The inner ends of the ports are disposed on the inner surfaces of the bearings 113 and 114, that is, the bearing surfaces, and the outer ends of the ports lead to the bearing air grooves 113' and 114' via ring-shaped passagees 119'.

Air supply branch ducts 121, 122 and 123, and exhaust duct 124 are formed in the head housing 111 of the main handpiece unit. All air supply branch ducts lead to the air supply passage 116, and the exhaust duct leads to an area formed between the inner surface of the exhaust passage 117 (in which the air supply passage 116 is disposed) and the outer surface of the air supply passage 116. The branch duct 123 is open at a nozzle 123' which faces the surfaces of turbine blades. Thus, a turbine 115 is rotated when air is jetted from the nozzle 123'. The exaust duct 124 is open facing the rear surface of the turbine blade. Thus, the air spent to rotate the turbine 115 is discharged from the exhaust duct 124 through the exhaust passage 117.

On the other hand, the air supply duct 121 leads to the upper bearing air groove 113' and the air supply duct 122 leads to the lower bearing air groove 114'. Therefore, air is fed from the air supply branch ducts 121 and 122 through the air supply ports 119 to clearances a and b formed between the external surface of the spindle 112 and the internal surfaces of the bearings 113 and 114. By the air, the spindle 112 is separated from the bearing contact surface of the spindle 112 and floated in the air to cope with the load applied to the spindle 112 in the radial direction.

The clearance c between the upper surface of the turbine 115 and the lower surface of the upper bearing 113, and the clearance d between the lower surface of the turbine 115 and the upper surface of the lower bearing 114 lead to the clearances a and b respectively as well as the exhaust duct 124. As a result, the air fed to the clearances a and b is further fed to the clearances c and d. Thus, the turbine 115 is separated and floated in the thrust direction to cope with the load applied in the thrust direction.

Referring to the control circuit diagram in FIG. 1 (b), a compressed air source 141 and a fixed-amount pressure regulating valve 143 are disposed along the air supply passage 116 in the same way as those of the conventional system. However, unlike the conventional system, a flowrate regulating device 144 is disposed between atmosphere and a handpiece 100 along the exhaust passage 117. The rotation speed of the air turbine 115 is decreased by throttling the flowrate regulating device 144. In this case, pressure P in the formula (4) is increased so that the decrease of mass flowrate g per unit time can be minimized to ensure rotation speed control with low decrease of torque T. The flowrate regulating device 144 can be fully closed to stop the turbine 115. To perform such a rotation speed control with low decrease of torque, the exhaust passage 117 has an airtight construction free of leakage at least in the range between the exhaust duct 124 and the regulating device 144 and also free of air bleeding to an air/water mixture passage 127 for removing chips from teeth as shown in FIGS. 1 (a), 2 (a) and 2 (b). Air to the air/water mixture passage 127 is supplied from a different system line.

Since the rotation speed is controlled by throttling the exhaust passage, air supply pressure Po in the air supply passage 116 is maintained high and thus the especially small radial clearances a and b of the air bearings 113 and 114 are securely maintained. Unlike the conventional system, the bearing performance is maintained high.

In the air supply passage 116, a three-way solenoid valve 128 is disposed to open/close the air supply passage and to purge remaining compressed air. The three-way solenoid valve 128 is controlled by an ON-OFF switch 129a which is activated when the operator presses the foot pedal of a foot controller 129. FIG. 1 (c) is a control circuit diagram of another control device of the present invention. Unlike the control device shown in FIG. 1 (b), a remote-controlled variable throttle valve 144' (pressure regulating valve) is disposed in parallel to the flowrate regulating valve 144" along the exhaust passage 117. To control the rotation speed of the turbine 115, exhaust pressure is adjusted by adjusting a motor-activated variable throttle valve 144' using the variable resistor or other means in the foot controller 129 via a control circuit 131 while the flowrate regulating valve 144" is opened at a constant degree. The rotation speed of the turbine 115 can also be controlled in a limited low or high speed range by adjusting the flowrate regulating valve 144". The flowrate regulating valves 144' and 144" in FIGS. 1 (b) and (c) can be replaced with a pressrue regulating valve to perform the same rotation speed control.

Figure 6:
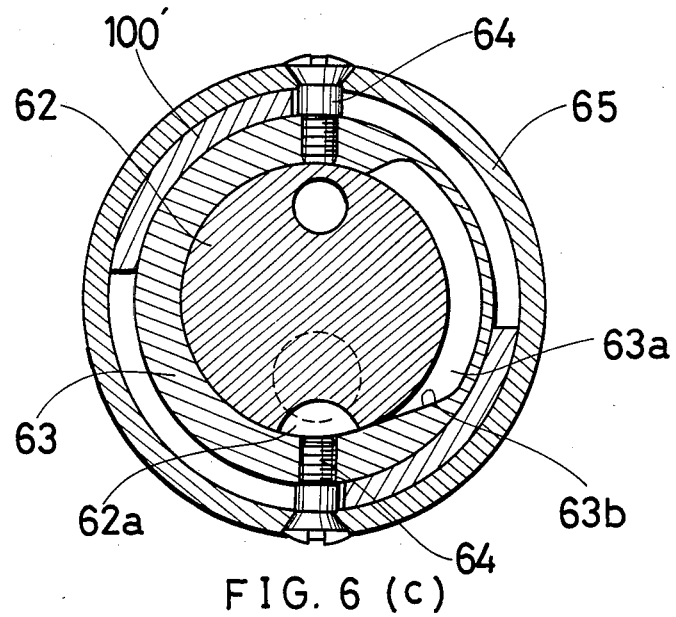
FIG. 6 (a) is a vertical sectional view of the connection section between the handpiece and the exhaust tube along the exhaust passage when the first mode of the regulating device is disposed.
Figure 6:
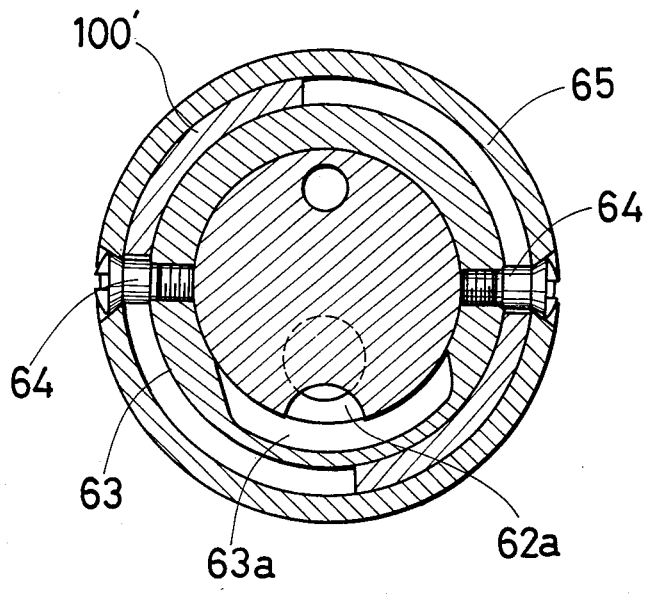

The flowrate regulating device 144 disposed in the exhaust passage 117 is installed at the first position, that is, the handpiece 100' as shown in FIGS. 1 (a), 3, 4 (a) and 5 (a), the second position, that is, the connection section between the exhaust passage 117' and the handpiece 100' (an adaptor 60 or 70 of the connection section) as shown in FIGS. 6 (a) and 7, the third position, that is, a connection section 85 between the exhaust tube 117' and a control means 81 disposed in the backboard of a dental bed 80, or the fourth position, that is, a control means 81 installed in the backboard of the dental bed. One of the flowrate regulating devices 144 shown in FIGS. 3, 4 (a), 5 (a), 6 (a) and 7 is properly selected and installed in each position.

Figure 3:
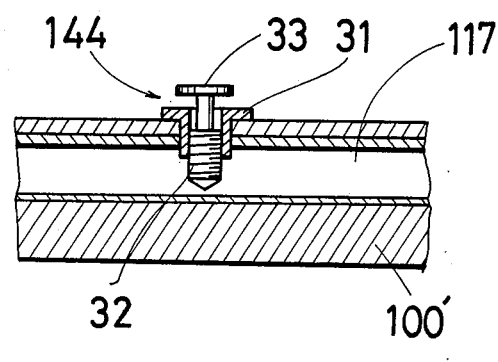
FIG. 3 is a detailed vertical sectional view illustrating of the first mode of the regulating device wherein the flowrate regulating device used in the first and second embodiments is disposed in the exhaust passage of the handpiece body.

FIG. 3 shows the first mode of the flowrate regulating device 144 disposed at the first position, that is, the handpiece 100'. The flowrate regulating device comprises a sleeve 31 which is hermetically fit in a hole passing from the external surface of the handpiece 100' to the exhaust passage 117, a valve unit 32 engaged with the screw on the internal surface of the sleeve and a knob 33 which is used to rotate the valve unit 32. The valve unit 32 is moved verticaly to the axis of the exhaust passage by turning the knob 33 and thus the flow area of exhaust air in the exhaust passage is changed. This flowrate regulating device is suited to steplessly change exhaust pressure.

Figure 4:
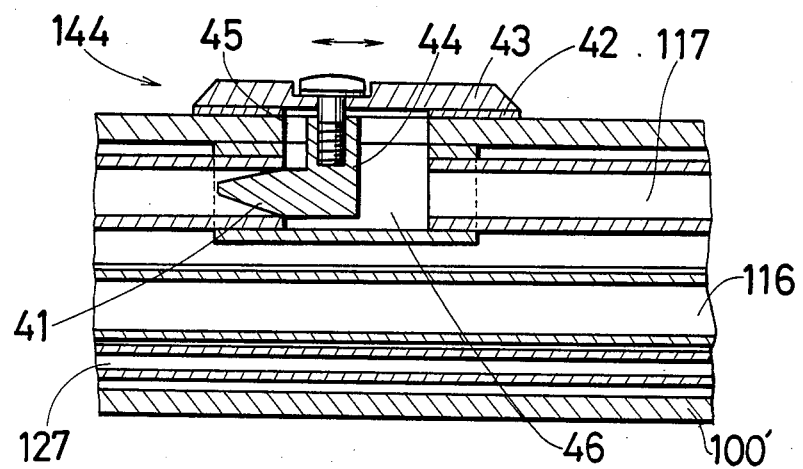
FIG. 4 (a) is a detailed vertical sectional view illustrating the second mode of the regulating device used at the same position as described above.
Figure 4:
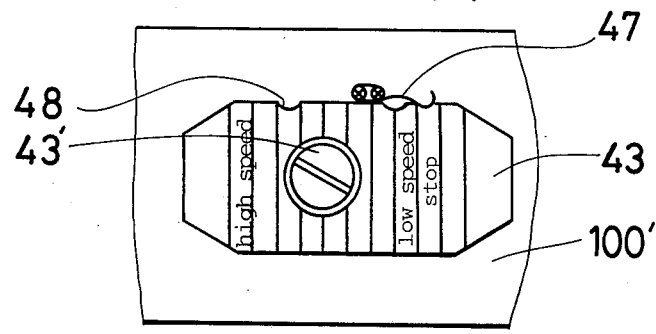

FIGS. 4 (a) and 4 (b) show the second mode of the flowrate regulating device 144 which is disposed at the handpiece 100'. This flowrate regulating device comprises a cone-shaped valve unit 41 which is coaxially fit in the exhaust passage 17, a knob 43 which has a circular cross section and is installed on the external surface of the handepiece 100' via an airtight packing 42 and a connecting rod 44 which connects the knob 43 to the valve unit 41. The connecting rod 44 is moved back and forth along a slot 45 in the longitudinal direction of the handpiece 100' to change the flow area of exhaust air in the exhaust passage 117.

The valve unit 41 and the connecting rod 44 are disposed in a hollow section 46 whose inner diameter is larger than that of the exhaust passage. The knob 43 is shifted between the high-speed and low-speed positions and also to the stop position by engaging a spring 47 with notches 48, located on the side of the knob 43. It is easily understood that the knob 43 can be steplessly moved by placing a belleville spring under the head of a screw 43'.

Figure 5A:
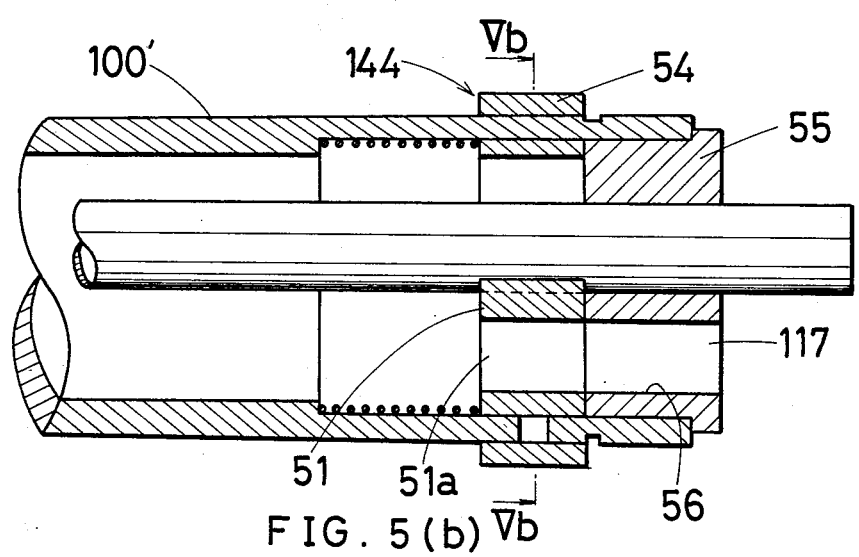
FIG. 5 (a) is a vertical sectional view of the third mode of the regulating device used at the same position as described above.
FIG. 5(b) is a sectional view taken substantially along the line Vb—Vb of FIG. 5 (a)
Figure 5B:
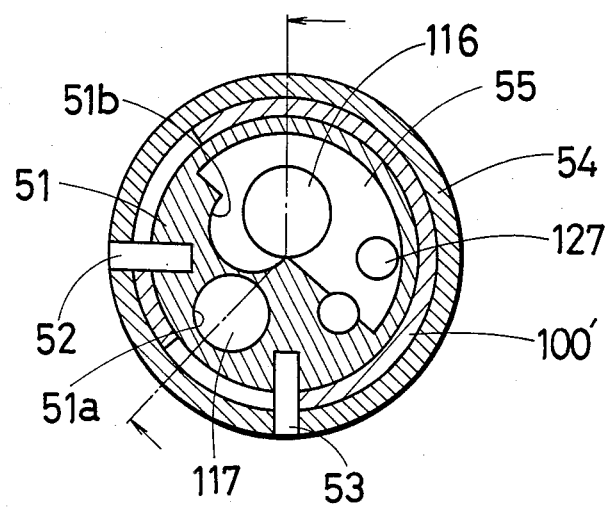

FIGS. 5 (a) and 5 (b) show the third mode of the flowrate regulating device 144. This flowrate regulating device 144 comprises a semi-circular shutoff plate 51 which is disposed crosswise to the exhaust passage 117 and is rotatable along the internal wall surface of the handpiece, a control ring 54 which is disposed around the handpiece and is connected to the shutoff plate 51 via rotation limitation pins 52 and 53. The shutoff plate 51 has a through hole 51a which completely aligns with an exhaust hole 56 in the end wall 55 of the handpiece at the full-open position (high-speed position) and a semi-circular cutout 51b which prevents the shutoff plate 51 from interfering the air supply passage. This flowrate regulating device has a stepless adjustment construction as shown in FIG. 5 (b). However, the device can also have a construction for step-by-step adjustment.

The first mode of the flowrate regulating device 144 installed at the second position, that is, an adaptor located at the connection section between the handpiece 100' and the exhaust tube 117' is explained as described below.

As shown in FIGS. 6 (a), 6 (b) and 6 (c), this flowrate regulating device 144 has an opening section 62a which leads to the exhaust passage 117 and is located o the circumferential surface of the core 62 of the adaptor 60 connected to the handpiece 100' via a sleeve joint 61. To control the opening degree of the opening section 62a using a cutout groove 63a disposed inside the ring 63 which is rotatably fit in the core 62, the ring is connected via connection pins to the control ring 65 which is mounted around the adaptor and is slidable in the circumferential direction. The control ring 65 is used to control the exhaust pressure. A conduit 69 including the exhaust tube 117' is connected to the adaptor 60 via a "one-touch" joint 68. FIG. 6 (b) shows the stop condition obtained when the exhaust opening 62a section is completely closed, and FIG. 6 (c) shows the high-speed condition obtained when the exhaust opening section 62a is fully opened. The taper section 63b of the cutout groove 63a is used to steplessly control the speed.

Figure 7:
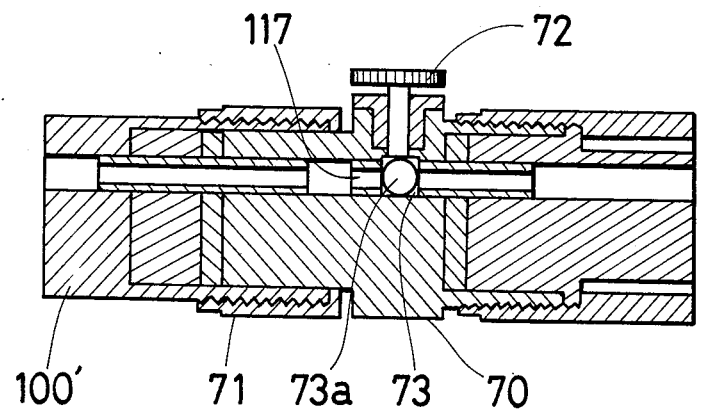
FIG. 7 is a detailed vertical sectional view of the second mode of the regulating device used at the same place as described above.

The construction shown in FIG. 7 can also be used as the second mode of the flowrate regulating device 144 installed at the second position. In this construction, the exhaust passage 117 of the adaptor 70 connected to the handpiece 100' via a sleeve joint 71 is closed by a cylindrical valve 73 which is airtightly supported so that the valve 73 can be rotated using a knob 72.

The valve 73 has a through hole 73a which coaxially aligns with the exhaust passage 117 when the valve is fully opened. The opening degree of the valve is regulated by turning the knob 72. This is suited for stepless control of rotation speed.

Figure 8:
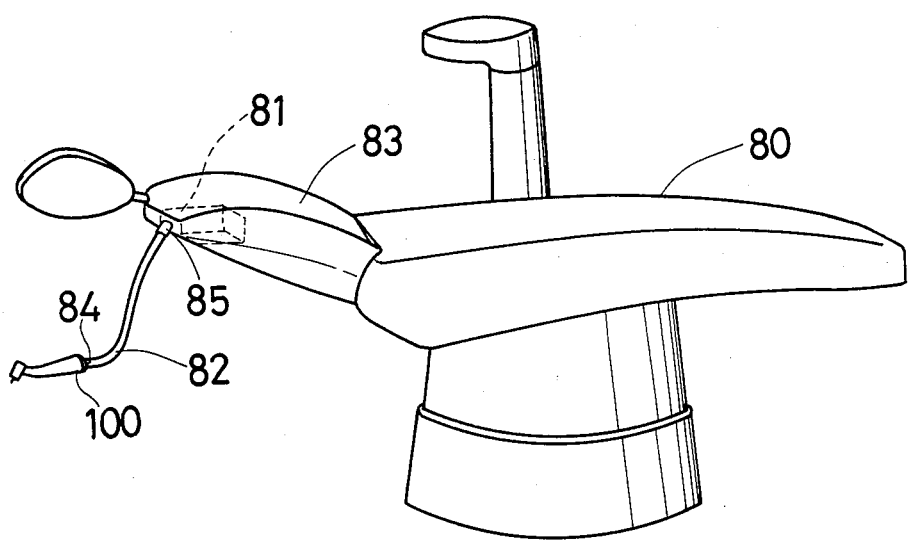
FIG. 8 is a drawing to explain the connection section between the exhaust tube and the control means and to explain the control means as a different position for disposing the regulating device.

The adaptors 60 and 70 with the flowrate regulating device at the second position can also be disposed at the third position, that is, the connection section 85 between a control means 81 (disposed in the backboard or a unit table of a dental bed 80) and a conduit 82 including the exhaust tube by changing the sleeve joint as shown in FIG. 8. It is easily understood that the two modes of the flowrate regulating devices 144 at the first and second positions can be easily installed in the exhaust passage 117 located inside the control means 81 located at the fourth position.

Figure 9:
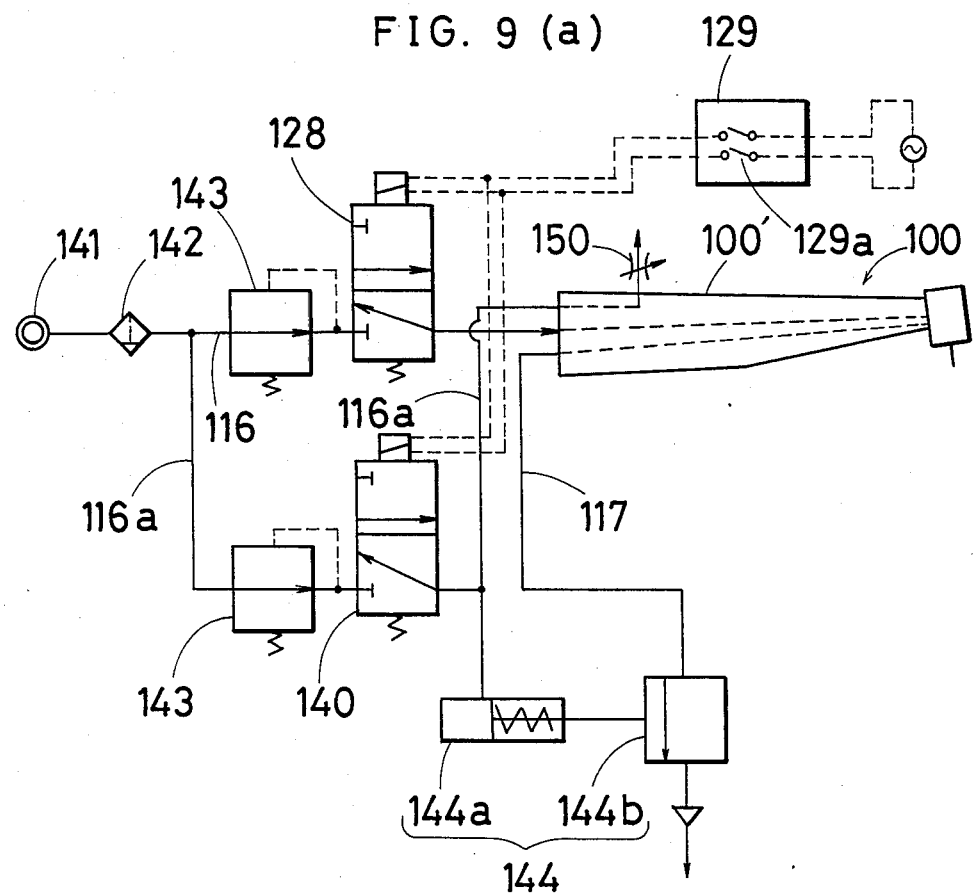
FIG. 9 (a) is a control circuit diagram of the third embodiment of the present invention.
Figure 9C:
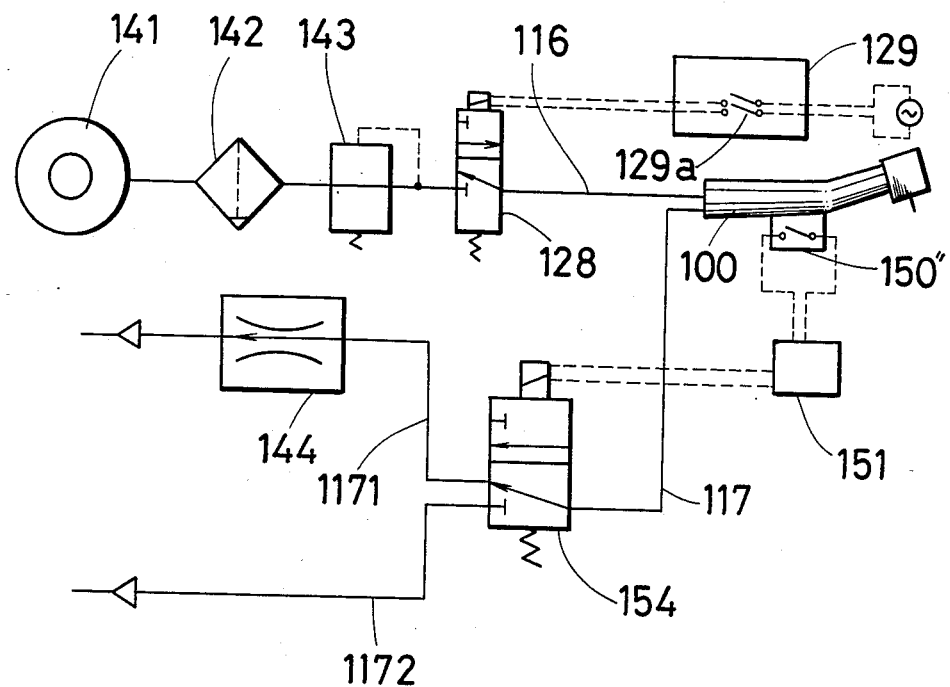
Figure 9:
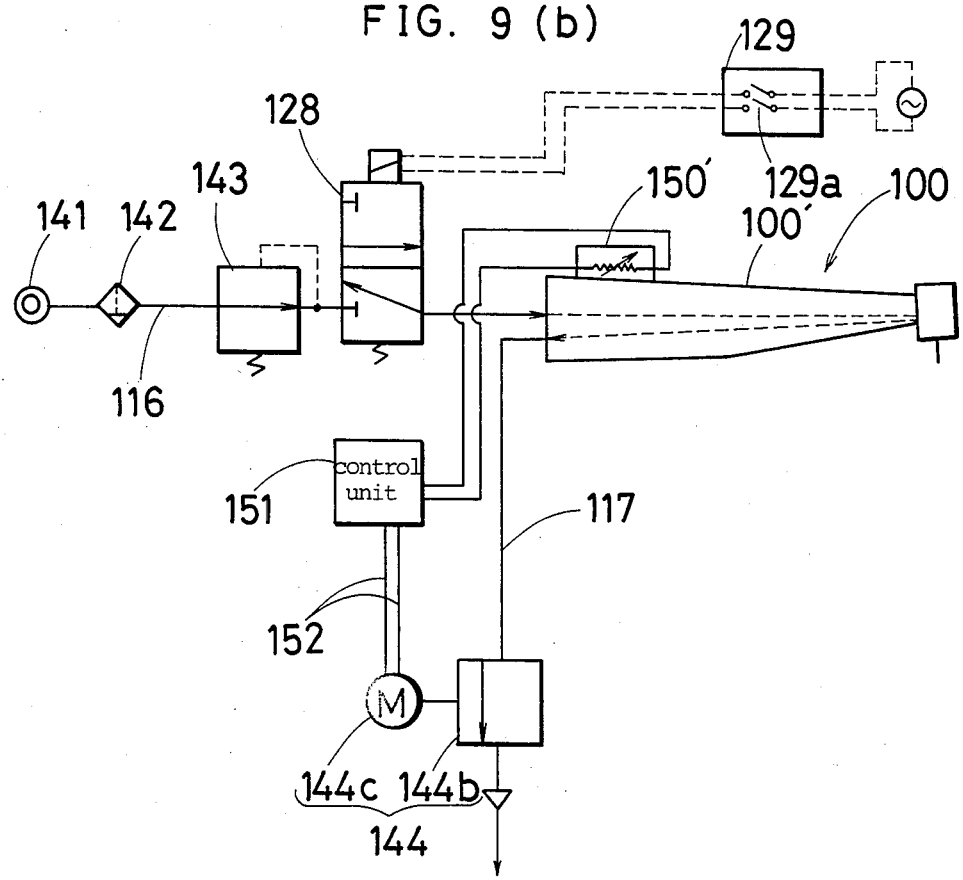

FIG. 9 (a) is a rotation speed control circuit diagram of the third embodiment of the present invention.

Like the conventional system, the compressed air source 141, filter 142, reducing valve 143 and selection valve 128 are disposed along the air supply passage 116. However, unlike the conventional system, the flowrate/pressure regulating device 144 which controls the rotation speed of the air turbine is disposed in the exhaust passage 117. The flowrate/pressure regulating device 144 comprises a servomechanism including a pneumatic cylinder 144a and a flowrate regulating valve 144b whose opening degree is controlled by the stroke control of the servomechanism. Compressed air is supplied to the pneumatic cylinder 144a through a pilot air supply passage 116a branched from the air supply passage 116 and the stroke of the pneumatic cylinder 144a is controlled by controlling air pressure in the pilot air supply passage 116a using an external control means such as a variable air throttle valve 150. In the pilot air supply passage 116a, a reducing valve 143 and a selection valve 140 are disposed to reduce the pressure of the branched air to a pilot air pressure, that is, a constant pressure suited for control of the pneumatic cylinder 144a. In this embodiment, the variable air throttle valve 150 is disposed in the handpiece 100' and is used to fine-regulate and remote-control the flowrate regulating valve 144b of the flowrate/pressure regulating device 144 via the pilot air supply passage 116a. Although the flowrate/pressure regulating device 144 can be disposed at any desired position along the exhaust passage 117 from the air turbine to atmosphere, the device is preferably disposed along the exhaust passage 117 in the control means 81 located in the backboard 83 of the dental bed 80 as shown in FIG. 8 so that the device can be remote-controlled. The variable air throttle valve 150, an external control means, can be disposed inside the handpiece 100, that is, at the connection section 84 between the handpiece 100' and the conduit 82 including an exhaust tube, at the connection section 85 between the conduit 82 and the control means 81 or in the control means 81 as shown in FIG. 8 so that the operator can conveniently regulate the valve. FIG. 9 (b) is a control circuit diagram of the fourth embodiment of the present invention. The construction of the air supply passage 116 is the same as that of the third embodiment. However, the opening degree of the flowrate regulating valve 144b disposed in the exhaust passage 117 is controlled by the electric servomechanism of a servomotor 144c or other means. An AC servomotor, DC servomotor or stepping motor can be used as the servomotor 144c. The rotation direction, angle and speed of the servomotor is controlled by the input voltage controlled by a variable resistor 150' (external control means) installed in the handpiece 100' and a control unit 151 connected to the motor via a control line 152. The positions of the flowrate/pressure regulating device 144 and external control means 150' are the same as those of the third embodiment. These two embodiments are operated as described below. The operation switch 129a generally installed in a controller 129 is turned on, selection valves 128 and 140 are turned on, and compressed air is supplied to the air supply passage 116 and the pilot air supply passage 116a of the handpiece 100, and the air turbine is operational. However, since the flowrate regulating valve 144b disposed in the exhaust passage 17 is fully opened, compressed air flows and the turbine rotates at high speed. The rotation speed of the air turbine is reduced by gradually opening the flowrate regulating valve 144b using the external control means 150'.

FIG. 9 (c) is a control circuit diagram of the fifth embodiment of the present invention. The construction of the air supply passage 116 of the fifth embodiment is the same as that of the third embodiment. However, unlike the third embodiment, the selection valve 154 disposed in the exhaust passage 117 can select a high-speed passage 1172 which does not have any flowrate regulating valve or a low-speed passage 1171 which has the fixed-amount flowrate regulating valve 144, using a selection switch 150" via a control circuit 151. With this construction, the operator can select high-speed cutting or low-speed cutting using the selection switch. Although a solenoid valve is used for the selection valve and an electric switch is used for the selection switch in the embodiment, a pneumatic selection valve and a pneumatic switch can also be used as a matter of course. Although two passages are used for selection in the embodiment, three passages can also be used for selection of high-speed, middle-speed or low-speed. In this way, step-by-step control can be performed by using the construction of the fifth embodiment.

Figure 11A:
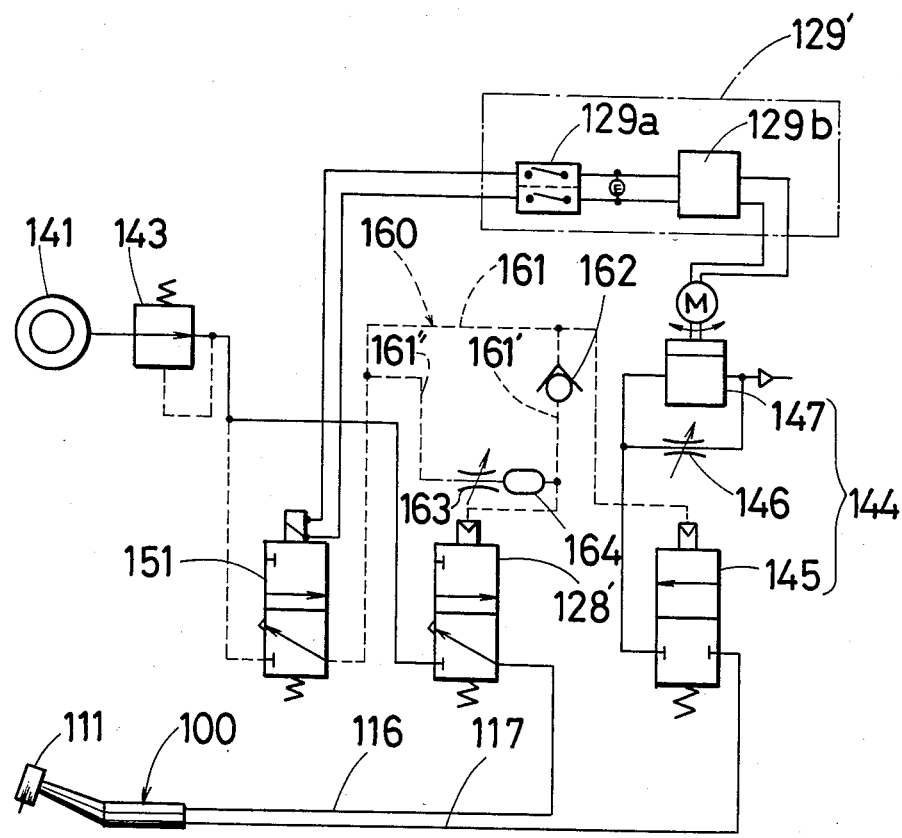
FIG. 11 (a) is a control circuit diagram of the sixth embodiment of the present invention suited for rapid stop control.
Figure 11B:
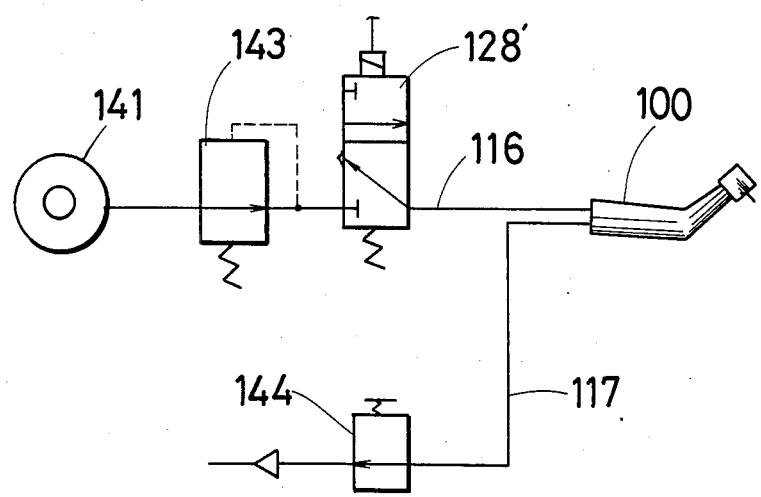
Figure 13:
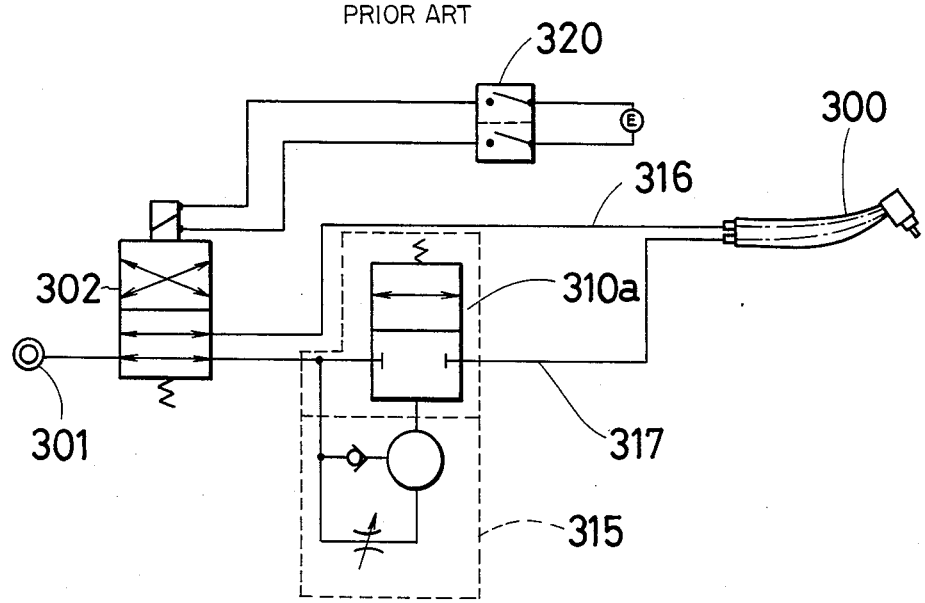
FIG. 13 is a control circuit diagram of the conventional handpiece.

FIG. 11 (a) is a control circuit diagram of the sixth embodiment of the present invention, which is suited for rapid stop. Air supplied from the compressed air source 141 passes through a filter (not shown), a reducing valve 143, a 3-port, 2-position selection valve 128' which functions as a pilot valve and the air suply passage 116 and reaches the handpiece 100. Then, the air is further supplied to the bearings 113 and 114 and the turbine 115 via the air supply branch ducts 121, 122 and 123 as described above.

Exhaust air spent for rotation of the turbine 115 flows from the exhaust duct 124 through the exhaust passage 117, the pilot valve 145 of the flowrate/pressure regulating device 144 and a parallel connection of a variable throttle valve 146 and a servo valve 147 and to atmosphere. The exhaust passage 117 leading to the servo valve 147 is extremely airtight and free of bleeding. The rotation speed can be controlled depending on the pressing stroke of a foot controller 129' which comprises a servomotor controll circuit 129b and an ON/OFF switch 129a which turns on when the foot controller is pressed and turns off when released.

In the servomotor control circuit 129b, the pressing stroke is converted into a pulse signal for example and controls the opening degree of the servo valve 147 which includes a stepping motor whose speed is proportional to the number of input pulses. Stopping the air turbine 115 begins when the foot controller 129' is released. First, the ON/OFF switch 129a turns off and thus the power to the 3-port, 2-position selection valve 151 which functions as the main control valve for controlling supply of compressed air to a timer circuit 160 and the pilot valve 128' is stopped. As a result, supply of compressed air is immediately shut off by spring force. Accordingly, the control pressure to the valve 145 along the exhaust passage 117 drops and the valve is set to the OFF position by spring force and then the exhaust passage 117 is closed. Thus, the air turbine 115 is rapidly stopped as described in the operating principle.

During the time between the release of the foot controller 129' and the rapid stop of the turbine, compressed air remains fed to the handpiece 100 via the pilot valve 128' which is controlled by the timer circuit 160 so that the bearings 113 and 114 can properly function in the radial direction until the turbine 115 stops completely. The timer circuit 160 comprises a check valve 162 disposed in a branch pipe 161' which joins a pilot valve 144 from a control air pipe 161 extending from a main control valve 151 to an opening valve 145 and is parallelly branched, a variable throttle valve 163 disposed in another branch pipe 161' and an air tank 164. When the ON/OFF switch 129a is turned on and the handpiece 100 is operated, compressed air from the compressed air source 141 fills the air tank. While the ON/Off switch 129a is turned off and the turbine is braked, the pilot valve 128' is kept open by the compressed air filled in the air tank 164. When braking begins and the ON/OFF switch 129a is turned off, the main control valve is activated to discharge the compressed air from the air tank 164 to atmosphere through the throttle valve 163, and the pilot valve 128' is also activated by spring force to release compressed air remaining in the air supply passage 116, the handpiece 100 and the exhaust passage 117 to atmosphere. This prevents the handpiece 100 from being uncontrollably operated by residual compressed air.

The control circuit of the seventh embodiment shown in FIG. 11 (b) is more simplified and has no timer circuit. The circuit is suited for rapid stop of a constant-speed handpiece. Rapid stop is performed by closing a two-port, 2-position selection valve 144 (flowrate regulating device) along the exhaust passage 117. A three-port, 2-position selection valve 128' in the air supply passage 116 is mainly used for start control. This timer releases residual compressed air after the lapse of stop time determined by a timer circuit similar to that used in the control circuit of the sixth embodiment.

Figure 10:
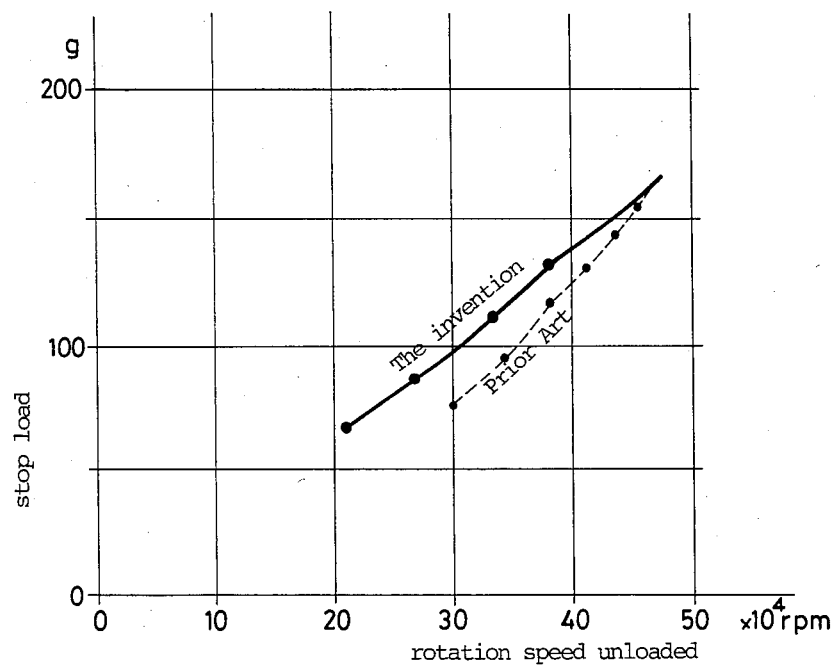
FIG. 10 is a graph illustrating the rotation torque increased by the control device of the dental handpiece of the present invention.
Figure 12:
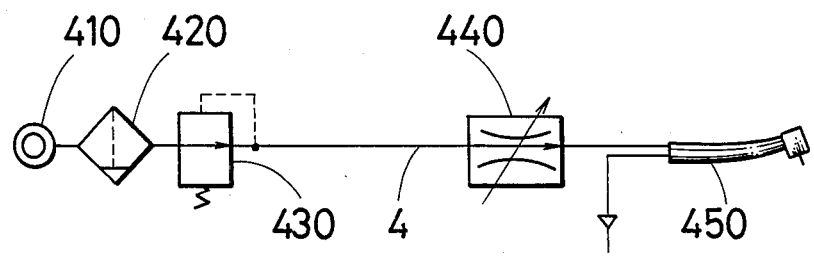
FIG. 12 is a control circuit diagram of the conventional handpiece.

As described above, the air turbine handpiece control device of the present invention controls exhaust air pressure using the pressure regulating device or flowrate regulating device 144 and the variable throttle valve 130 disposed along the exhaust passage 117 to control the speed of the air turbine 115. In addition, as detailed in the explanation of the operating principle, rotation torque T greater than that of the conventional supply air pressure control system is obtained as the turbine speed is lowered by increasing the throttling degree (see the graph in FIG. 10). Therfore, this feature is especially effective for treatment which needs large torque at low speed. The experiment results shown in FIG. 10 were obtained by the method frequently used to measure the rotation torque of dental handpieces. The stop load along the vertical axis of the graph is a rotation stop load (unit: g) of a test bar of 1.6 mm in diameter.

The turbine 115 is rapidly stopped by completely shutting off the exhaust passage 117 using the pressure/flowrate regulating device 144 disposed in the exhaust passage 117 and by generating negative rigidity on the bearing thrust surfaces. Air is kept supplied until the turbine rapidly stops so that the pneumatic bearings 113 and 114 can maintain their bearing functions in the radial direction.

Therefore, the rotation performance and load performance of the handpiece 100 is not impaired.

Furthermore, since the air pressure in the housing 111 is kept high, counterflow of external air is prevented and entry of foreign matter into the bearing section is also prevented. Thus, the durability of the pneumatic bearing type dental handpiece can be greatly improved. The rapid stop of a cutting tool after operation significantly increases safety. Moreover, by releasing air pressure remaining after the turbine 115 is stopped using the selection valve 128' disposed along the air supply passage 116, the handpiece 100 is prevented from being uncontrollably operated by residual compressed air. This further increases the safety of the handpiece.

Still more, by disposing a pressure/flowrate regulating device in the handpiece 100 in the exhaust passage 117, the connection section between the handpiece and the exhaust passage 117, the connection section 85 between the exhaust passage and the control means 81, or the control means, the speed control of the handpiece can be conveniently performed at a position close to the operator so that proper and accurate treatment is ensured.

As mentioned in the explanation of the third, fourth and fifth embodiments, the external control means 150, 150', 150" for controlling the opening degree of the flowrate/pressure regulating device 144 is disposed in the handpiece 100', the connection section 84 between the handpiece and exhaust tube 82, the connection section 85 between the exhaust tube 82 and the control means 81, or the control means 81. As a result, the speed control of the handpiece can be more conveniently performed at a position close to the operator, and proper and accurate treatment is ensured.

We claim:

1. A control device for use in a handpiece comprising an air turbine which is integrated with a spindle supporting a cutting tool and is rotatably supported in a head housing via pneumatic bearings, an air supply passage which supplies compressed air to said air turbine, and a non-bleeding exhaust passage which discharges air spent to drive said air turbine, said control device being characterized in that said control device comprises a flowrate regulating device disposed in said exhaust passage to change the back pressure of said air turbine, said air supply passage comprises a three-port, two position selection valve to open and close said air supply passage for releasing residual compressed air by controlling said air supply passage and a timer circuit for controlling said three-port, two position selection valve and said exhaust passage comprises a valve for opening and closing said exhaust passage, and a control circuit which opens said air supply passage during a specified time between completion of turbine stop operation and actual stopping of said turbine, closes said three-port, two position selection valve after said specified time has passed, and close said exhaust passage when stop operation begins.

2. A control device according to claim 1, wherein said flowrate regulating device is controlled by a foot controller.

3. A control device according to claim 1, wherein an external control means for remote-controlling the opening degree of said flow rate regulating device is disposed in said handpiece.

4. A control device according to claim 1, wherein an external control means for remote-controlling the opening degree of said flow rate regulating means is disposed in the connection section between said handpiece and an exhaust tube.

5. A control device according to claim 1, wherein an external control means for remote-controlling the opening degree of said flow rate regulating means is disposed in the connection section between said exhaust tube and a control means.

6. A control device according to claim 1, wherein an external control means for remote-controlling the opening degree of said flow rate regulating device is disposed in said control means.

7. A control device according to claim 4, 5, or 6, wherein said external control means is a variable throttle valve which controls pilot air pressure, that is, an input signal supplied to a servomechanism which activates said flowrate regulating device.

8. A control device according to claim 4, 5, or 6 wherein said external control means is a variable resistor which controls an input voltage, that is, an input signal fed to said servomechanism which activates said flowrate regulating device.

9. A control device according to claim 4, 5, or 6, wherein said external control means is selection switch which controls an input signal to a selection valve which selectively activates one of a plurality of said flowrate regulating devices.

10. A control device according to claim 1, wherein said flow rate regulating device is disposed along said exhaust passage in said handpiece.

11. A control device according to claim 1, wherein said flow rate regulating device is disposed along said exhaust passage in the connection section between said handpiece and said exhaust tube.

12. A control device according to claim 1, wherein said flow rate regulating device is disposed along said exhaust passage in the connection section between said exhaust tube and said control means.

13. A control device according to claim 1, wherein said flow rate regulating device is disposed along said exhaust passage in said control means.

14. A control device according to claim 11, 12 or 13 wherein said flowrate regulating device comprises a valve unit which is rotatably supported by a knob and is moved vertically to the axis of said exhaust passage along a screw engagement section to change the flow area of exhaust air in said exhaust passage.

15. A control device according to claim 1 or 11, 12, or 13, wherein said flowrate regulating device comprises a cone-shaped valve unit which is coaxially fit in said exhaust passag and is moved together with a knob along the axis of said exhaust passage to change the flow area of exhaust air in said exhaust passage, and a connecting rod for connecting said knob and said valve unit which is disposed in a hollow section whose inner diameter is larger than that of said exhaust passage.

16. A control device according to claim 1 or 11, 12 or 13, wherein said flowrate regulating device comprises an almost semi-circular shutoff plate rotatably disposed in and crosswise to said exhaust passage, said shutoff plate having a through hole which coaxially aligns with an exhaust hole at the fullopen position so that the opening degree of said exhaust hole is adjusted by said through hole which is controlled by rotating said shutoff plate using an external control ring.

17. A control device according to claim 1 or 10, wherein said flowrate regulating device comprises a ring which is rotatably fit in a core with an opening section leading to said exhaust passage and being located on the circumferential surface of said core, said ring having a cutout groove disposed inside said ring so that the opening degree of said opening section is controlled by said ring using an external control ring.

* * * * *